United States Patent [19]

Marquis et al.

[11] 4,252,981

[45] Feb. 24, 1981

[54] SYNTHESIS OF METHYLENE BIS(METHYLANTHRANILATE)

[75] Inventors: Edward T. Marquis; Ernest L. Yeakey, both of Austin, Tex.

[73] Assignee: Texaco Development Corp., White Plains, N.Y.

[21] Appl. No.: 99,779

[22] Filed: Dec. 3, 1979

[51] Int. Cl.[3] .......................................... C07C 101/68
[52] U.S. Cl. ..................................................... 560/48
[58] Field of Search ......................................... 560/48

[56] References Cited

PUBLICATIONS

Tsirul'Nikova et al., Chem. Absts., 86, 72137(y), 1977.
Khofbauer et al., Chem. Absts., 74, 125086(s), 1971.

*Primary Examiner*—Natalie Trousof
*Assistant Examiner*—G. T. Breitenstein
*Attorney, Agent, or Firm*—Carl G. Ries; Robert A. Kulason; James L. Bailey

[57] ABSTRACT

Covers a process for the production of methylene bis(-methylanthranilate) which comprises the steps of condensing methylanthranilate with formaldehyde in the presence of a siliceous catalyst.

3 Claims, No Drawings

SYNTHESIS OF METHYLENE BIS(METHYLANTHRANILATE)

BACKGROUND OF THE INVENTION

1. Field of the Invention

This invention relates to the manufacture of methylene bis(methyl anthranilate).

2. Description of the Prior Art

Methylene bis(methyl anthranilate) has been found useful as an amine-type curing agent in a number of applications such as in curing epoxy resins or as a chain-extender in urethane formulations. The compound is most often prepared by reacting formaldehyde with methylanthranilate in the presence of acetic acid to produce an intermediate product. The acetic acid is then removed by either distillation or neutralization and HCl is then added to rearrange the intermediate to obtain the methylene bis(methyl anthranilate). Again the hydrochloric acid has to be removed by neutralization.

The disadvantages of employing the just described scheme are obvious. In the first place there are handling drawbacks as well as safety considerations involved in the use of the two liquid acids. Secondly, the acids must necessarily be neutralized leading to unwanted salt production, which salt must necessarily be disposed of in an environmentally safe manner. Again, one must resort to relatively expensive corrosion resistant equipment, particularly when employing a strong acid such as hydrochloric acid. Lastly, as just described the overall process is multi-step in nature adding to the overall expense.

It would therefore be a distinct advance in the art if methylene bis(methyl anthranilate) could be made in an efficient, one-step process without necessary resort to use of corrosive acids which must be subsequently neutralized in order to properly isolate the desired product. Other objects will appear hereinafter.

SUMMARY OF THE INVENTION

This invention comprises a convenient process of preparing methylene bis(methyl anthranilate) which comprises the step of condensing methylanthranilate with formaldehyde in the presence of a siliceous catalyst such as a silica-alumina catalyst.

DETAILED DESCRIPTION OF THE INVENTION

When one employs a siliceous solid catalyst the overall reaction proceeds in a convenient one-step process, leading directly to the methylene bis(methyl anthranilate). The siliceous catalyst is then filtered from the product, and (either reused, if sufficiently active or disposed of-the volume being manageable) normally reused.

In order to produce the desired product at least two moles of methylanthranilate per mole of formaldehyde are employed. In the usual case a molar excess of methylanthranilate is employed. Thus the ratio of methylanthranilate to formaldehyde usually ranges from about 2:1 up to about 6:1, and more often falls within the range of 2-4 moles of methylanthranilate per mole of formaldehyde.

The solid siliceous catalyst may be chosen from a wide variety of materials of this type including silica-alumina and other acid clays and easily filtratable acidic catalysts such as phosphoric acid on silica. Usually the amount of catalyst will range from about 0.01 up to about 4% based on the weight of the reactants. More often the amount of catalyst employed is 0.01-3% based on the reaction mass.

The reaction may be effected at atmospheric pressures or super- or sub-atmospheric pressure. Usually the reaction is carried out under a pressure ranging from about 50 psig to about 2000 psig.

Again, the temperature of reaction may range rather widely depending upon other variables such as pressure, type of catalyst employed and formaldehyde to methylanthranilate mole ratio. However, usually, the temperature of the reaction ranges from about 100° C. to about 300° C.

Again, the reaction may be carried out with or without benefit of solvent. If a solvent is employed, usually it is an aqueous media or mixed water-hydrophilic organic solvent media.

By employing the catalyst here the process is carried out in a simple one-step technique. Moreover, there is no neutralization required with concomitant salt removal and disposal problems. Any corrosion problem involved in using a strong acid such as hydrochloric acid is eliminated. The catalyst itself can be simply removed by merely filtering the hot reaction product. Lastly, since one may carry out the reaction in carbon steel equipment versus relatively more expensive corrosion resistant equipment, the overall process economics are greatly improved.

The following example typically illustrates the process of the invention. It is understood, of course, that this example is given by way of illustration and not as a limitation upon the scope of the invention.

EXAMPLE I

Preparation of methylene bis(methyl anthranilate)III.

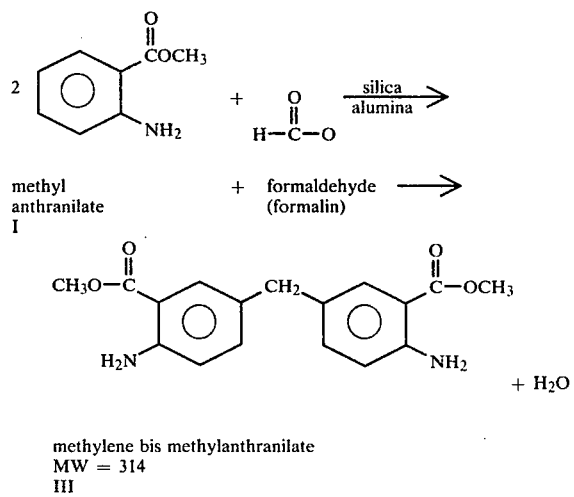

To a 1-liter, stirred, stainless steel autoclave was added 604 grams of methyl anthranilate (4.0 moles, obtained from Sherwin Williams Corp.), 75 ml. of 37% formalin (1.0 mole of formaldehyde) and 18.1 grams of AEROCAT® Silica Alumina TA (American Cyanamid Co.). The clave was flushed with nitrogen, sealed and heated to 200° C. and held there for 3 hours with stirring. The reaction mixture was filtered hot to remove catalyst and stripped to remove water and unreacted methyl anthranilate. The stripping took place under high vacuum (1–2 mm) and went to a 200° C. pot temp. The product remaining after stirring amounted to 275.0 grams. Yield=275/314=88%.

The product had a total titratable amine content of 6.42 meq./g. (Theory=6.37 meg/g) Infrared and nuclear magnetic resonance spectra support the structure III. Gel permeation chromatography indicates 96.59% of the product to be a material with a molecular size similar to dimeric product III and 3.41% to be of a smaller species.

The invention is hereby claimed as follows:

1. A process for the production of methylene bis(methyl anthranilate) which comprises the steps of condensing methylanthranilate with formaldehyde in the presence of a siliceous catalyst selected from the group consisting of silica-alumina and other acid clays and phosphoric acid on silica.

2. The process of claim 1 wherein said siliceous catalyst is a silica-alumina catalyst.

3. The process of claim 1 which is carried out at a temperature ranging from about 100° C. to about 300° C. under superatmospheric pressures ranging from about 50 psig to about 2000 psig.

* * * * *